US012788801B2

(12) United States Patent
Kristensen

(10) Patent No.: US 12,788,801 B2
(45) Date of Patent: Nov. 10, 2026

(54) TREATMENT OF HYPERURICEMIA

(71) Applicant: Frederiksberg Hospital, Frederiksberg C (DK)

(72) Inventor: Lars Erik Vølund Kristensen, Vedbæk (DK)

(73) Assignee: FREDERIKSBERG HOSPITAL, Frederiksberg C (DK)

( * ) Notice: Subject to any disclaimer, the term of this patent is extended or adjusted under 35 U.S.C. 154(b) by 1043 days.

(21) Appl. No.: 17/997,832

(22) PCT Filed: May 5, 2021

(86) PCT No.: PCT/EP2021/061886
§ 371 (c)(1),
(2) Date: Nov. 3, 2022

(87) PCT Pub. No.: WO2021/224338
PCT Pub. Date: Nov. 11, 2021

(65) Prior Publication Data

US 2023/0173032 A1 Jun. 8, 2023

(30) Foreign Application Priority Data

May 7, 2020 (EP) .................................... 20173380

(51) Int. Cl.
*A61K 38/26* (2006.01)
*A61P 19/06* (2006.01)

(52) U.S. Cl.
CPC .............. *A61K 38/26* (2013.01); *A61P 19/06* (2018.01)

(58) Field of Classification Search
None
See application file for complete search history.

(56) References Cited

U.S. PATENT DOCUMENTS

2011/0046076 A1 2/2011 Eickehnann et al.
2013/0035281 A1 2/2013 Klein et al.
2014/0087996 A1 3/2014 Klein et al.

FOREIGN PATENT DOCUMENTS

WO 1998/08871 A1 3/1998
WO 2011/032175 A1 3/2011
WO WO-2012100748 A1 * 8/2012 .............. A61P 29/00
WO WO2012107476 A1 8/2012

OTHER PUBLICATIONS

Tonneijck (Diabetes Obes Metab. May 2018 ; 20(5): 1235-1245). (Year: 2018).*
Tonneijck (Diabetes Care. Nov. 2016;39(11):2042-2050. Epub Sep. 1, 2016). (Year: 2016).*
Jacobson (downloaded from https://pharmacy.ucsf.edu/news/2015/07/study-discovers-why-leading-gout-medication-ineffective-many; published Jul. 14, 2015) (Year: 2015).*
Chen et al., Hypercuricemia-related diseases and xanthine oxidoreductase (XOR) inhibitors: an overview, Med Sci Monit, 22: 2501-2512, 2016.
Fan et al., Therapeutic efficacy of liraglutide on diabetic nephropathy mice by inhibiting inflammatory factors, European Journal of Inflammation, 16: 1-6, 2018.
Gudbergsen et al., Effect of liraglutide on body weight and pain in the treatment of overweight and knee osteoarthritis: A randomised, double-blind, placebo-controlled study, BMJ: 71-72, 2019.
International Search Report and Written Opinion issued in PCT/EP2021/061886 on Aug. 2, 2021.
Ishii et al., Improvement of quality of life through glycemic control by liraglutide, a GLP-1 analog, in insulin-naive patients with type 2 diabetes mellitus: the PAGE1 study, Diabetol Metab Syndr, 9:3, 2017.
Lofty et al., The effect of glucagon-like peptide-1 in the management of diabetes mellitus: cellular and molecular mechanisms, Cell and Tissue Research, 358: 343-358, 2014.
Nielsen et al., Weight loss for overweight and obese individuals with gout: a systematic review of longitudinal studies, Ann Rheum Dis, 76(11):1870-1882, 2017.
Richette et al., 2016 updated EULAR evidence-based recommendations for the management of gout, Ann Rheum Dis, 76:2 9-42, 2017.
Tonneijck et al., Effect of immediate and prolonged GLP-1 receptor agonist administration on uric acid and kidney clearance: Post-hoc analyses of four clinical trials, Diabetes, Obesity and Metabolism, 20(5): 1235-1245, Jan. 11, 2015.
Chino, et al., SGLT2 inhibitor lowers serum urlc acid through alteration of uric acid transport activity in renal tubule by increased glycosuria, Biopharmaceuticals and Drug Disposition, 35: 391-404, Aug. 6, 2014.
Chui, et al., Evaluation of Clinical Value and Safety of Combined Therapy with Liraglutide and Insulin Aspart 30 in the Treatment of Refractory Type 2 Diabetes Mellitus, Guide of China Medicine, 16(31): 134-135, Nov. 2018.
English translation of Chinese Office Action for Chinese Application No. 2021800329394, dated Sep. 25, 2024.
English translation of Chinese Search Report for Chinese Application No. 2021800329394, dated Sep. 25, 2024.
Packer, M., Hyperuricemia and Gout Reduction by SGLT2 Inhibitors in Diabetes and Heart Failure, Journal of American College of Cardiology, 83(2): 371-381, Jan. 16, 2024.
Yin, Dong-Sheng, Effect of liraglutide in the treatment of diabetes complicated with hyperuricemia, Clinical Medicine Research and Practice, pp. 47-48, Oct. 2019.

(Continued)

*Primary Examiner* — Brian Gangle
*Assistant Examiner* — Andrea K Mccollum
(74) *Attorney, Agent, or Firm* — Weston R. Gould; DINSMORE & SHOHL LLP

(57) ABSTRACT

The present invention relates to methods for treatment of hyperuricemia using glucagon-like peptide-1 receptor agonists. The invention is based on a double-blinded, placebo controlled study in overweight and obese patients where a significant urate lowering was observed in subjects with increased serum urate levels.

18 Claims, 3 Drawing Sheets

(56) References Cited

OTHER PUBLICATIONS

Jiang et al., The influence of exenatide in blood uric acid levels of type 2 diabetes patients with asymtomatic hyperuieaemia, Chongquing Medicine, 22: 3066-3068, 2016.

Mandell, B. "Allopurinol hypersensitivity is rare, bad, and partially avoidable, but allopurinol can still be used effectively." Cleveland Clinic Journal of Medicine. vol. 92. No. 6. Jun. 2025. 326-328.

* cited by examiner

TREATMENT OF HYPERURICEMIA

CROSS REFERENCE TO RELATED APPLICATIONS

This application is a U.S. National Stage of international application PCT/EP2021/061886 filed May 5, 2021, which claims priority to European Application No: 20173380.5 filed May 7, 2020, the entire contents of each of which are incorporated herein by reference.

TECHNICAL FIELD

The present invention relates to methods for treatment of hyperuricemia using GLP-1 receptor agonists.

BACKGROUND

Hyperuricemia is a condition of high serum total urate levels. In humans and higher primates, uric acid is the final oxidation product of purine catabolism. In most other mammals, however, the enzyme uricase further oxidizes uric acid to allantoin. In human and higher primates, which lack the enzyme uricase, purine metabolites such as xanthine and hypoxanthine are oxidized by xanthine oxidase to uric acid. In humans, the upper end of the normal range is 360 μmol/L (6 mg/dL) for women and 400 μmol/L (6.8 mg/dL) for men. The presence of total urates including uric acid in the serum is important and beneficial because these compounds are potent antioxidants. In humans, about half the antioxidant capacity of plasma comes from total urates including uric acid.

On the other hand, high serum total urate levels, or hyperuricemia, are often associated with several maladies. For example, high serum total urate levels can lead to a type of arthritis in the joints known as gout. Gout is a condition created by a build-up of monosodium urate or uric acid crystals on the articular cartilage of joints, tendons and surrounding tissues due to elevated concentrations of total urate levels in the blood stream. The build-up of urate or uric acid on these tissues provokes an inflammatory reaction of these tissues. Saturation levels of uric acid in urine may result in one form of kidney stones when the uric acid or urate crystallizes in the kidney. These uric acid stones are radiolucent and so do not appear on an abdominal x-ray. Therefore, their presence must be diagnosed by ultrasound. Some patients with or without gout eventually develop uric kidney stones. Additionally, high serum total urate levels are often associated with acute and chronic uric acid nephropathy, and the so-called metabolic syndrome, including cardiovascular disease and hypertension.

Conventionally, it was believed that high total urate levels are merely innocuous or could even be beneficial because of the antioxidant activity of uric acid. More recently, however, this view has been challenged. Rather, it has been proposed that total urates are a true risk factor for cardiovascular disease and hypertension. Thus, there is evidence that high serum total urate level, or hyperuricemia, is a risk factor for hypertension.

Hyperuricemia is caused either by accelerated generation of total urates and uric acid through purine metabolism or by impaired excretion of total urates in the urine. Consumption of purine-rich diets is one of the causes of hyperuricemia. High levels of fructose in the diet may also cause hyperuricemia. Other dietary causes are ingestion of high protein and fat, and starvation. Starvation results in the body metabolizing its own muscle mass for energy, in the process releasing purines into the bloodstream. Hyperuricemia may lead to renal diseases and may also exacerbate existing renal conditions.

In recent years, the prevalence of hyperuricemia has significantly increased and more clinical investigations have confirmed that hyperuricemia is an independent risk factor for cardiovascular disease, hypertension, diabetes, and many other diseases. Urate-lowering therapy may also play a critical role in the management of these diseases. However, current Xanthine-Oxidoreductase-inhibitor drugs such as allopurinol and febuxostat may have significant adverse effects.

SUMMARY

The current inventor has demonstrated through double-blinded, placebo controlled clinical studies in overweight and obese subjects that the GLP-1 Receptor Agonist (GLP-1-RA) Liraglutide can lead to clinically relevant reduction in serum urate levels in subjects with increased serum urate. The effect appears to be independent of the weight lowering effect of Liraglutide.

Case studies with administration of Semaglutide to normoglycemic patients with high serum urate showed similar effects on lowering of urate levels.

A separate dietary intervention clinical study with obese patients with gout confirmed that despite a significant weight loss, there was no statistical difference in effect on the the serum urate levels compared to patients receiving standard dietary advice. In other words, the effects demonstrated by Liraglutide and Semaglutide are not caused by their effect on weight loss.

Thus the inventor has provided a safe alternative to the existing urate lowering drugs. As GLP-1-RAs are generally known to treat type 2 diabetes, cardiovascular risk reduction, and in some cases also weight loss, the current invention provides yet another beneficial effect of GLP-1-RAs on a severe disorder.

In a first aspect, the disclosure relates to a glucagon-like peptide-1 receptor agonist for use in the treatment of hyperuricemia in a subject.

In other aspects the disclosure relates to a method of treatment of hyperuricemia by administering a therapeutically effective amount of a GLP-1 receptor agonist to a subject in need thereof.

The disclosure further relates to use of a GLP-1 receptor agonist for the preparation of a medicament for the treatment of hyperuricemia and to a pharmaceutical composition or a medicament comprising a GLP-1 receptor agonist in the treatment of hyperuricemia.

In a preferred embodiment the subject suffering from hyperuricemia is normoglycemic, or has a normal HbA1C level.

The GLP-1 receptor agonist may be selected from Exenatide, Liraglutide, Lixisenatide, Albiglutide, Dulaglutide, and Semaglutide. The GLP-1 receptor agonist may be a dual GLP-1-GIP receptor agonist, such as Tirzepatide or it may be a dual GLP-1-Glucagon receptor agonist.

In preferred embodiments, the GLP-1 receptor agonist is Liraglutide and the dosage is from 1 to 3 mg liraglutide once per day, such as 1.2-1.8 mg, preferably 3 mg. Administration is preferably via subcutaneous injection.

Liraglutide is approved for weight reduction at a dosage of 3 mg once per day and for reduction of cardiovascular risk at a dosage of 1.2 to 1.8 mg once per day. In both cases, the treatment is initiated using a dose escalation until the end level is reached.

DEFINITIONS

Figure 1:
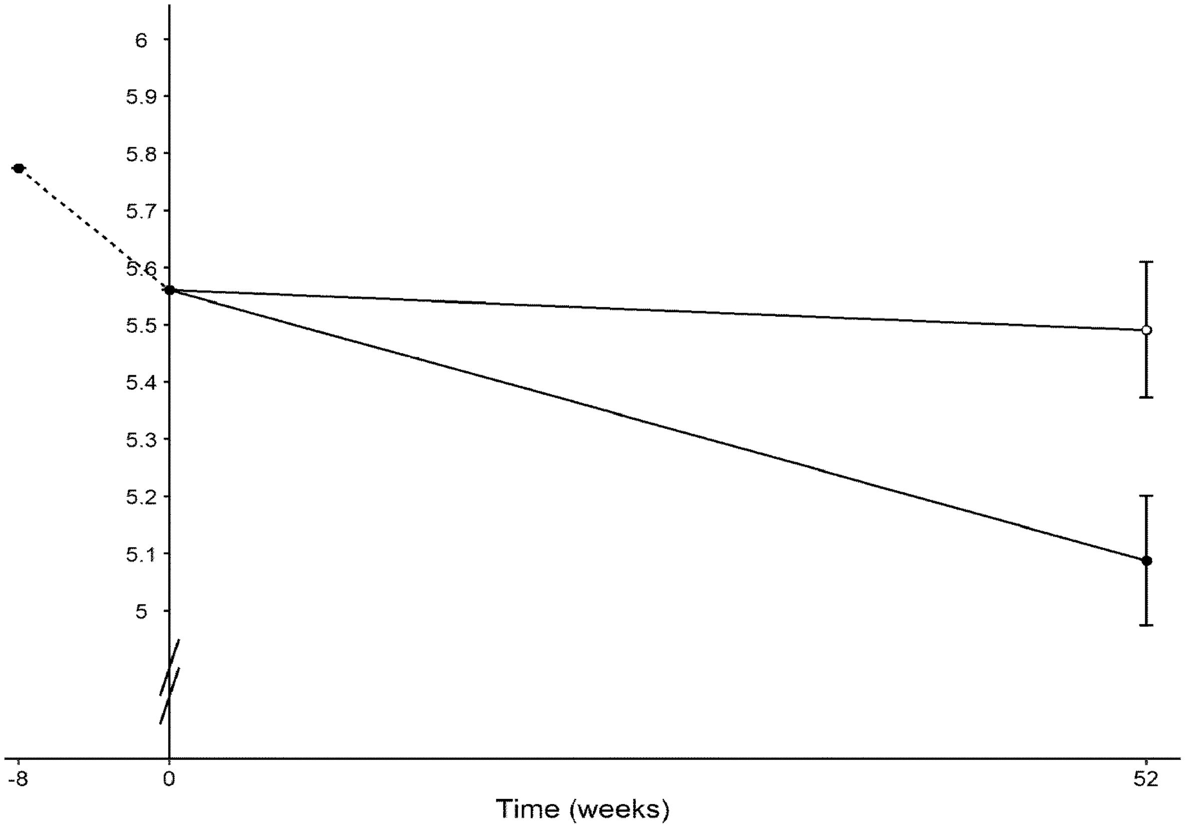
FIG. 1: Serum urate in mg/dL at different timepoints (weeks). Estimates are unadjusted means at week −8 and 0 (dotted line; n=155) and least square means estimates from an ANCOVA model (adjusted for stratification factors, i.e. sex, age category, obesity class as well as the level of the outcome at baseline) for data at 52 weeks (solid lines; n=134). Solid points at week 52 indicate the liraglutide group (n=69) and open points indicate the placebo group (n=65). The error bars indicate SE.

"Normal glucose levels" is used interchangeably with the term "normoglycemic" and "normal" and refers to a fasting venous plasma glucose concentration of less than 6.1 mmol/L (110 mg/dL). Although this amount is arbitrary, such values have been observed in subjects with proven normal glucose tolerance, although some may have IGT as measured by oral glucose tolerance test (OGTT). Glucose levels above normoglycemic are considered a pre-diabetic condition.

As used herein, the term "hyperuricemia" denotes a disease state in which the patient has as an elevation in serum urate (sUA) levels greater than or equal to 6.0 mg/dL in women and men. Many factors contribute to hyperuricemia, including: genetics, insulin resistance, hypertension, renal insufficiency, obesity, diet, use of diuretics, and consumption of alcoholic beverages. Causes of hyperuricemia can be classified into three functional types: increased production of uric acid, decreased excretion of uric acid, and mixed type, incorporating both of the previous etiologies. Increased production etiologies result from high levels of purine in the diet and increased purine metabolism. Decreased excretion etiologies result from kidney disease, certain drugs, and competition for excretion between uric acid and other molecules. Mixed causes include high levels of alcohol and/or fructose in the diet, and starvation. Hyperuricemia typically develops into gout when urate crystals are formed from supersaturated body fluids and deposited in joints, tophi, and parenchymal organs due to a disorder in the urate metabolism. Uric acid is the end product of purine metabolism and is generated in the cascade of hypoxantine→xanthine→uric acid.

The term "GLP-1 receptor agonist" (GLP-1-RA) in the scope of the present invention includes, without being limited, exogenous GLP-1 (natural or synthetic), GLP-1 analogues and other substances (whether peptidic or non-peptidic, e.g. small molecules) which promote signalling through the GLP-1 receptor. The exogenous GLP-1 includes natural and synthetic GLP-1, in particular human GLP-1. The GLP-1 analogues include longer acting analogues also which are resistant to or have reduced susceptibility to enzymatic degradation, for example by DPP-4 and/or NEP 24.11. The term includes dual and triple GLP-1 receptor agonists which additionally agonize the glucagon receptor and dual GLP-1-RAs that additionally agonise the GIP receptor. Examples of approved GLP-1-receptor agonists include Exenatide, Liraglutide, Lixisenatide, Albiglutide, Dulaglutide, and Semaglutide.

The terms "treatment" and "treating" as used herein refer to the management and care of a patient for the purpose of combating a condition, disease or disorder. The term is intended to include the full spectrum of treatments for a given condition from which the patient is suffering, such as administration of the active compound for the purpose of: alleviating or relieving symptoms or complications; delaying the progression of the condition, disease or disorder; curing or eliminating the condition, disease or disorder; and/or preventing the condition, disease or disorder, wherein "preventing" or "prevention" is to be understood to refer to the management and care of a patient for the purpose of hindering, postponing or reducing the disease to prevent, postpone or reduce the risk of the onset of symptoms or complications. The patient to be treated is preferably a mammalian, in particular a human being, male or female. The patients to be treated can be of various ages.

DETAILED DESCRIPTION

Serum uric acid (SUA) concentration is a significant parameter for human health. Alteration of SUA homeostasis has been linked to a number of diseases. For example, an abnormally high SUA level, termed hyperuricemia, is the underlying cause of gout and has been correlated with cardiovascular disease, hypertension, and renal disease. More recent studies have demonstrated that hyperuricemia may directly contribute to the development or progression of these diseases. Besides gout, therapies that directly inhibit the production of uric acid may be effective to prevent and/or treat hyperuricemia-related cardiovascular disease and other diseases.

High uric acid levels can lead to urate crystallization, oxidative stress, inflammation and endothelial dysfunction.

Chen et al 2016 (Hypercuricemia-related diseases and xanthine oxidoreductase (XOR) inhibitors: an overview, Med Sci Monit 22: 2501-2512) lists hyperuricemia as an independent risk factor for gout, kidney stone, renal failure (acute or chronic urate nephropathy), hypertension, atherosclerosis, ischemic heart disease, heart failure, stroke, type 2 diabetes, metabolic syndrome, and nonalcoholic fatty liver disease. Thus uric acid is a central player, not an innocent bystander, in cardiovascular disease and many other diseases.

In certain embodiments, the subject is a human being, such as an adult human being. In still other embodiments, the subject suffers from gout and/or renal failure.

The present disclosure describes methods for the reduction of total serum urate and the treatment of gout, renal failure and other diseases associated with hyperuricemia.

In another aspect, the treatment of hyperuricemia in a subject comprises administering to the mammal in need of said treatment a therapeutically effective amount of a GLP-1-RA and an inhibitor of uric acid synthesis, in where the uric acid synthesis inhibitor is administered before, after or simultaneously with the GLP-1-RA.

The effect observed in the appended example is largest in the group having the highest serum urate levels. Therefore, it is preferred that the subject has a serum level of uric acid above 6 mg/dL prior to initiation of treatment, such as above 6.5 mg/dL, for example above 6.8 mg/dL, or above 7 mg/dL.

The treatment may be effective to lower the uric acid level by at least 0.1 mg/dL over 8 weeks, such as at least 0.2 mg/dL, for example at least 0.3 mg/dL or more over 8 weeks.

In other embodiments, the treatment results in reduction in the number and severity of flares. In still further embodiments VAS (visual analogue scale) pain and VAS fatigue is reduced in the subject.

A visual analogue scale (VAS) is a psychometric response scale which can be used in questionnaires. It is a measurement instrument for subjective characteristics or attitudes that cannot be directly measured. When responding to a VAS item, respondents specify their level of agreement to a statement by indicating a position along a continuous line between two end-points.

The urate lowering effects demonstrated are expected to lead to one or more of the following: reduction in joint pain, joint effusion, joint erosion (including joint space narrowing or joint cartilage degradation), deposits of uric acid crystals, and deposition of uric acid in joints.

GLP-1-RAs

Preferred GLP-1-RAs to be used according to the present disclosure are currently approved GLP-1-RAs Exenatide, Liraglutide, Lixisenatide, Albiglutide, Dulaglutide, and Semaglutide, preferably Liraglutide or Semaglutide.

Liraglutide is the GLP-1 receptor agonist Arg34, Lys26-(N-epsilon-(gamma-L-glutamyl(N-alfa-hexadecanoyl)))-GLP-I(7-37). Liraglutide may be prepared as described in Example 37 of WO 98/08871.

Exenatide, Liraglutide, Lixisenatide, Albiglutide, Dulaglutide, and Semaglutide may be administered in the form of a pharmaceutical composition. The pharmaceutical composition may comprise Exenatide, Liraglutide, Lixisenatide, Albiglutide, Dulaglutide, and Semaglutide, preferably Liraglutide in a concentration from 0.1 mg/ml to 100 mg/ml. In some embodiments the pharmaceutical composition comprises 0.01-50 mg, or 0.01-20 mg, or 0.01-10 mg/ml Exenatide, Liraglutide, Lixisenatide, Albiglutide, Dulaglutide, and Semaglutide, preferably Liraglutide. In some embodiments the pharmaceutical composition comprises 1-20 mg/ml Exenatide, Liraglutide, Lixisenatide, Albiglutide, Dulaglutide, and Semaglutide, preferably Liraglutide or Semaglutide.

The pharmaceutical compositions described herein may further comprise one or more pharmaceutically acceptable excipients, for example selected from the group consisting of buffer system, preservative, tonicity agent, chelating agent, stabilizer and surfactant. In some embodiments the pharmaceutical composition comprises one or more pharmaceutically acceptable excipients, such as one or more selected from the group consisting of a buffer, an isotonic agent, and a preservative. The formulation of pharmaceutically active ingredients with various excipients is known in the art, see e.g. Remington: The Science and Practice of Pharmacy (e.g. 19th edition (1995), and any later editions). The term "excipient" broadly refers to any component other than the active therapeutic ingredient(s), e.g. Exenatide, Liraglutide, Lixisenatide, Albiglutide, Dulaglutide, and Semaglutide, preferably Liraglutide, or Semaglutide. The excipient may be an inert substance, an inactive substance, and/or a not medicinally active substance.

In some embodiments the pharmaceutical composition comprises a phosphate buffer, such as a sodium phosphate buffer, e.g. disodium phosphate. In some embodiments the pharmaceutical composition comprises an isotonic agent, such as propylene glycol. In some embodiments the pharmaceutical composition comprises a preservative, such as phenol.

The pharmaceutical composition may be in the form of a solution or a suspension. In some embodiments the pharmaceutical composition is aqueous composition, such as an aqueous solution or an aqueous suspension. The term "aqueous composition" is defined as a composition comprising at least 50% w/w water. Likewise, the term "aqueous solution" is defined as a solution comprising at least 50% w/w water, and the term "aqueous suspension" is defined as a suspension comprising at least 50% w/w water. An aqueous composition may comprise at least 50% w/w water, or at least 60%, 70%, 80%, or even at least 90% w/w of water. In some embodiments the pharmaceutical composition has a pH in the range of 7.5-9.0.

In some embodiments Exenatide, Liraglutide, Lixisenatide, Albiglutide, Dulaglutide, and Semaglutide, preferably Liraglutide is administered in the form of a pharmaceutical composition comprising about 1-20 mg/ml Exenatide, Liraglutide, Lixisenatide, Albiglutide, Dulaglutide, or Semaglutide, preferably Liraglutide, about 2-15 mM phosphate buffer, about 2-25 mg/ml propylene glycol, about 1-18 mg/ml phenol, and has a pH in the range of 7.5-9.0. In some embodiments Exenatide, Liraglutide, Lixisenatide, Albiglutide, Dulaglutide, or Semaglutide, preferably Liraglutide is administered in the form of a pharmaceutical composition comprising about 6 mg/ml Exenatide, Liraglutide, Lixisenatide, Albiglutide, Dulaglutide, or Semaglutide, preferably Liraglutide, about 1.42 mg/ml disodium phosphate dihydrate, about 14.0 mg/ml propylene glycol, about 5.5 mg/ml phenol, and has pH of about 8.15. In some embodiments Exenatide, Liraglutide, Lixisenatide, Albiglutide, Dulaglutide, or Semaglutide, preferably Liraglutide is administered in the form of a pharmaceutical composition comprising 6 mg/ml Exenatide, Liraglutide, Lixisenatide, Albiglutide, Dulaglutide, or Semaglutide, preferably Liraglutide, 1.42 mg/ml disodium phosphate dihydrate, 14.0 mg/ml propylene glycol, 5.5 mg/ml phenol, and has pH of 8.15.

Exenatide, Liraglutide, Lixisenatide, Albiglutide, Dulaglutide, and Semaglutide, preferably Liraglutide may be administered in a therapeutically effective amount, such as an amount therapeutically effective to treat type 2 diabetes, reduce the risk of cardiovascular disease or induce weight loss. The therapeutically effective amount of Exenatide, Liraglutide, Lixisenatide, Albiglutide, Dulaglutide, and Semaglutide, preferably Liraglutide or Semaglutide can be assessed by a medical doctor. The dosage of Exenatide, Liraglutide, Lixisenatide, Albiglutide, Dulaglutide, and Semaglutide, preferably Liraglutide or Semaglutide may be in the range from 0.1 to 10 mg.

Exenatide, Liraglutide, Lixisenatide, Albiglutide, Dulaglutide, and Semaglutide, preferably Liraglutide may be administered once daily. In some embodiments Exenatide, Liraglutide, Lixisenatide, Albiglutide, Dulaglutide, and Semaglutide, preferably Liraglutide is administered once daily at any time in the day. Exenatide, Albiglutide, Dulaglutide, and Semaglutide may be administered once weekly. In some embodiments the daily dosage of Exenatide, Liraglutide, Lixisenatide, Albiglutide, Dulaglutide, and Semaglutide, preferably Liraglutide is in the range from 0.4 to 4.0 mg, such as in the range from 0.4 to 2.0 mg. In some embodiments the daily dosage of Exenatide, Liraglutide, Lixisenatide, Albiglutide, Dulaglutide, and Semaglutide, preferably Liraglutide is selected from the group consisting of 0.6, 1.2, and 1.8 mg. In some embodiments the daily dosage of liraglutide is 3.0 mg.

Some GLP-1 RAs are approved for daily administration and some for weekly administration. Semaglutide is approved for once weekly administration and is contemplated for use according to the present disclosure at dosages from 0.25 to 5 mg once weekly, preferably 0.5 to 2.5 mg weekly. Dosing is initiated at a low level and increased until efficacy is achieved. The examples herein provide proof of clinical effect at 0.5 mg once weekly. Dulaglutide is also approved for once weekly dosing and is contemplated for use according to the present disclosure at dosages of 0.25 to 5 mg weekly, preferably 0.5 to 1.5 mg weekly.

GLP1-RAs can be administered orally but at much higher dosages. For example Semaglutide is approved for treatment of T2DM at oral dosages of 7-14 mg daily. Daily dosages of Semaglutide and other GLP1-RAs is contemplated at dosages ranging from 1-25 mg daily, such as 5-15 mg daily.

In some embodiments the term "chronic treatment" as used herein with reference to Exenatide, Liraglutide, Lixisenatide, Albiglutide, Dulaglutide, and Semaglutide, preferably Liraglutide means administration in an amount and frequency to provide a therapeutic effect. In some embodiments the term "chronic treatment" as used herein with reference to Exenatide, Liraglutide, Lixisenatide, Albiglutide, Dulaglutide, and Semaglutide, preferably Liraglutide means once daily administration 0.4-4.0 mg, such as 0.6, 1.2, 1.8 mg, or 3.0 mg Exenatide, Liraglutide, Lixisenatide, Albiglutide, Dulaglutide, and Semaglutide, preferably Liraglutide or Semaglutide.

Exenatide, Liraglutide, Lixisenatide, Albiglutide, Dulaglutide, and Semaglutide, preferably Liraglutide may be administered via parenteral administration, for example subcutaneous injection. Exenatide, Liraglutide, Lixisenatide, Albiglutide, Dulaglutide, and Semaglutide, preferably Liraglutide or Semaglutide may be administered using a pen-injector, such as a 3 ml disposable pen-injector. Semaglutide is approved for oral administration and can be used as an oral or injectable form according to the present disclosure. Other GLP-1 receptor agonists may be formulated for oral administration using similar formulations.

In some embodiments, Exenatide, Liraglutide, Lixisenatide, Albiglutide, Dulaglutide, and Semaglutide, preferably Liraglutide or Semaglutide is administered as a chronic treatment for at least 6 months, such as for at least 9 months, for example at least 12 months or more, during which chronic treatment, serum urate level is decreased.

Exenatide, Liraglutide, Lixisenatide, Albiglutide, Dulaglutide, and Semaglutide, preferably Liraglutide or Semaglutide may be administered as an extended release formulation such as a formulation for administration once weekly.

Also included within the scope of the application are dual GLP-1-GIP receptor agonists, such as Tirzepatide and dual GLP-1-Glucagon receptor agonists.

Co-Treatment

GLP-1-RAs may be administered as an adjunctive therapy to subjects already being treated for hyperuricemia. In other embodiments, GLP-1-RA is used as a safe alternative to subject that have previously been treated with XOIs that have resulted in no effect or in side effects. The XOI may be allopurinol, febuxostat, or topiroxostat.

The result of a previous treatment may be hypersensitivity to allopurinol or treatment emergent adverse events during allopurinol treatment.

In other embodiments the subject has not responded to XOI therapy, such as allopurinol therapy.

In still other embodiments the subject does not receive SGLT2 inhibitor therapy.

As the subjects have normal blood glucose and $HbA_{1C}$, the subject is not expected to be on insulin or insulin-analog therapy.

Subjects

The subjects to be treated with the GLP-1 receptor agonist of the present disclosure is preferably a human being. The subject may or may not suffer from gout. The subject may have osteoarthrosis.

In preferred embodiments the subject has impaired kidney function, such as renal impairment. Existing urate lowering drugs may cause severe side effects for such subjects and are contraindicated.

In some embodiments, the subject is overweight or obese.

Obesity is defined herein as a medical condition in which excess body fat has accumulated to the extent that it may have an adverse effect on health, leading to reduced life expectancy and/or increased health problems in general. Thus, in one embodiment the subject to be treated is overweight or obese.

Body mass index (BMI) is a measure which compares weight and height. People are generally considered overweight or pre-obese if the BMI is between 25 and 30 and obese if the BMI is over 30. Morbidly obese subjects have a BMI over 35.

In one embodiment the subject has a BMI above 25 $kg/m^2$, such as above 30 $kg/m^2$, for example above 35 $kg/m^2$, such as above 40 $kg/m^2$.

In one embodiment the subject has a BMI above 30 $kg/m^2$.

In one embodiment the subject has a BMI above 35 $kg/m^2$.

Included within the scope of the present disclosure is the treatment of normoglycemic subjects. Normoglycemic is defined with reference to WHO's diabetes diagnostic criteria. Included within the scope of the disclosure is also treatment of subjects where the fasting glucose level has been reduced by e.g. metformin. In embodiments of the disclosure the subject is non-diabetic.

The inventor has determined that the effect of GLP-1 receptor agonist on the serum urate level is not mediated through lowering of blood glucose. The subjects enrolled in the clinical trial were not diabetic according to the WHO criteria. A few were treated with metformin and were diagnosed with type 2 diabetes by their general practitioner. Excluding these from the results (FIG. 3), shows that the effect is not mediated through glucose lowering.

The subject may have a fasting glucose level below 7.0 mmol/L, such as 6.5 mmol/L, preferably below 6.1 mmol/L, below 6.0, below 5.5, or below 5.0 mmol/L. The fasting glucose level may suitably be determined prior to treatment onset as the GLP-1-RAs lower fasting blood glucose.

Expressed as $HbA_{1C}$ level, this is suitably below 48 mmol/mol, such as below 46, for example below 42, such as below 40 mmol/mol.

The WHO diabetes diagnostic criteria are shown in the table below.

| Condition | 2 hour glucose* mmol/l (mg/dl) | Fasting glucose mmol/l (mg/dl) | $HbA_{1c}$ mmol/mol (DCCT %) |
|---|---|---|---|
| Normal | <7.8 (<140) | <6.1 (<110) | <42 (<6.0) |
| Impaired fasting glycaemia | <7.8 (<140) | ≥6.1 (≥110) & <7.0 (<126) | 42-46 (6.0-6.4) |

-continued

| Condition | 2 hour glucose* mmol/l (mg/dl) | Fasting glucose mmol/l (mg/dl) | $HbA_{1c}$ mmol/mol (DCCT %) |
|---|---|---|---|
| Impaired glucose tolerance | ≥7.8 (≥140) | <7.0 (<126) | 42-46 (6.0-6.4) |
| Diabetes mellitus | ≥11.1 (≥200) | ≥7.0 (≥126) | ≥48 (≥6.5) |

*Venous plasma glucose 2 hours after ingestion of 75 g oral glucose load

Items

In the following the disclosure is described as numbered items.

1. A glucagon-like peptide-1 receptor agonist for use in the treatment of hyperuricemia in a subject
2. The GLP-1 receptor agonist for the use of item 1, wherein the subject is normoglycemic, or has a normal HbA1C level.
3. The GLP-1 receptor agonist for the use of any of the preceding items, wherein the GLP-1 receptor agonist is selected from Exenatide, Liraglutide, Lixisenatide, Albiglutide, Dulaglutide, and Semaglutide, preferably Liraglutide or Semaglutide.
4. The GLP-1 receptor agonist for the use of any of the preceding items, wherein the GLP-1 receptor agonist is a dual GLP-1-GIP receptor agonist, such as Tirzepatide.
5. The GLP-1 receptor agonist for the use of any of the preceding items, wherein the GLP-1 receptor agonist is a dual GLP-1-Glucagon receptor agonist.
6. The GLP-1 receptor agonist for the use of any of the preceding items, wherein the subject does not suffer from gout.
7. The GLP-1 receptor agonist for the use of any of the preceding items, wherein the subject suffers from gout.
8. The GLP-1 receptor agonist for the use of any of the preceding items, wherein the subject is overweight or obese.
9. The GLP-1 receptor agonist for the use of any of the preceding items, wherein the subject has impaired kidney function.
10. The GLP-1 receptor agonist for the use of any of the preceding items, wherein the subject has osteoarthrosis.
11. The GLP-1 receptor agonist for the use of any of the preceding items, wherein the subject is or has been treated with a xanthine oxidoreductase inhibitor (XOI).
12. The GLP-1 receptor agonist for the use of any of the preceding items, wherein the subject has been or is treated with allopurinol.
13. The GLP-1 receptor agonist for the use of any of the preceding items, wherein the subject is hypersensitive to allopurinol.
14. The GLP-1 receptor agonist for the use of any of the preceding items, wherein the subject does not respond to XOI therapy, such as allopurinol therapy.
15. The GLP-1 receptor agonist for the use of any of the preceding items, wherein the subject does not receive SGLT2 inhibitor therapy.
16. The GLP-1 receptor agonist for the use of any of the preceding items, wherein the subject is not on insulin or insulin-analog therapy.
17. The GLP-1 receptor agonist for the use of any of the preceding items, wherein the subject has a fasting glucose level below 7.0 mmol/L, such as 6.5 mmol/L, preferably below 6.1 mmol/L, below 6.0, below 5.5, or below 5.0 mmol/L.
18. The GLP-1 receptor agonist for the use of any of the preceding items, wherein the subject has a HbA1C level below 48 mmol/mol, such as below 46, for example below 42, such as below 40 mmol/mol.
19. The GLP-1 receptor agonist for the use of any of the preceding items, wherein the subject is non-diabetic.
20. The GLP-1 receptor agonist for the use of any of the preceding items, wherein the subject has a serum level of uric acid above 6 mg/dL prior to initiation of treatment, such as above 6.5 mg/dL, for example above 6.8 mg/dL or above 7 mg/dL.
21. The GLP-1 receptor agonist for the use of any of the preceding items, wherein the uric acid level is reduced by at least 0.1 mg/dL over 8 weeks, such as at least 0.2 mg/dL, for example at least 0.3 mg/dL or more.
22. The GLP-1 receptor agonist for the use of any of the preceding items, wherein the treatment reduces joint pain, joint effusion, deposits of uric acid crystals, deposition of uric acid in joints.
23. The GLP-1 receptor agonist for the use of any of the preceding items, wherein the GLP-1 receptor agonist is Liraglutide and the dosage is from 1 to 3 mg liraglutide once per day, such as 1.2-1.8 mg, preferably 3 mg.
24. A method for reducing joint pain in a subject suffering from gout, the method comprising administering a therapeutically effective amount of a GLP-1-RA.
25. A method for reducing fatigue in a subject suffering from gout, the method comprising administering a therapeutically effective amount of a GLP-1-RA.
26. A method for reducing flares in a subject suffering from gout, the method comprising administering a therapeutically effective amount of a GLP-1-RA.
27. A method for reducing joint effusion in a subject suffering from gout, the method comprising administering a therapeutically effective amount of a GLP-1-RA.
28. A method for reducing deposits of uric acid crystals in a subject suffering from gout, the method comprising administering a therapeutically effective amount of a GLP-1-RA.
29. A method for reducing deposition of uric acid in joints in a subject suffering from gout, the method comprising administering a therapeutically effective amount of a GLP-1-RA.

The following non-limiting Examples illustrate the advantageous properties of the compositions.

EXAMPLES

Example 1: Clinical Trial of Liraglutide

Background: There is an association between gout and obesity. Lowering urate is the cornerstone of gout management [1] and urate levels correlate with central obesity. Previous studies suggest that weight loss has a positive effect on serum urate, however, the studies are sparse and small [2].

Objectives: To assess the impact of an initial low-calorie diet-induced weight loss and subsequent randomisation to the body weight-lowering drug liraglutide (a glucagon-like peptide 1 receptor agonist) or placebo on serum urate levels.

Methods: In the LOSE-IT trial (NCT02905864), a randomised, double-blinded, placebo-controlled, parallel group, single-centre trial [3], 156 overweight and obese individuals with knee joint pain, were offered an initial 8-week intensive diet intervention (week −8 to 0) on Cambridge Weight Plan (800-1000 kcal/day) followed by a weight loss maintenance period in which participants were randomised to either liraglutide 3 mg/day or placebo for 52 weeks. Subjects with type 1 diabetes or type 2 diabetes with glucose-lowering drugs other than metformin were excluded from the study.

We conducted a secondary analysis of blood samples collected at week −8, 0 and 52. The primary outcome measure was change in serum urate. A clinical review showed that a subset of patients included fulfilled 2015 ACR/EULAR criteria for gout. We used paired t-test for the change from week −8 to 0, and for change from week 0 to 52 we used an ANCOVA model adjusted for stratification factors (sex, age category and obesity class), and the level of the outcome at baseline. Data were analysed as observed (i.e. no imputation of missing data).

Results: 156 individuals were randomised and 155 had blood samples taken at baseline. At baseline, the patient population fasting median glucose level was 5.8 mmol/L (SD 1.17) and the HbA1C value was 37.5 mmol/mol (SD 4.27). In the initial intensive diet intervention period (week −8 to 0) they lost a mean of 12.5 kg (95% CI −13.1 to −11.9, n 156).

Figure 2:
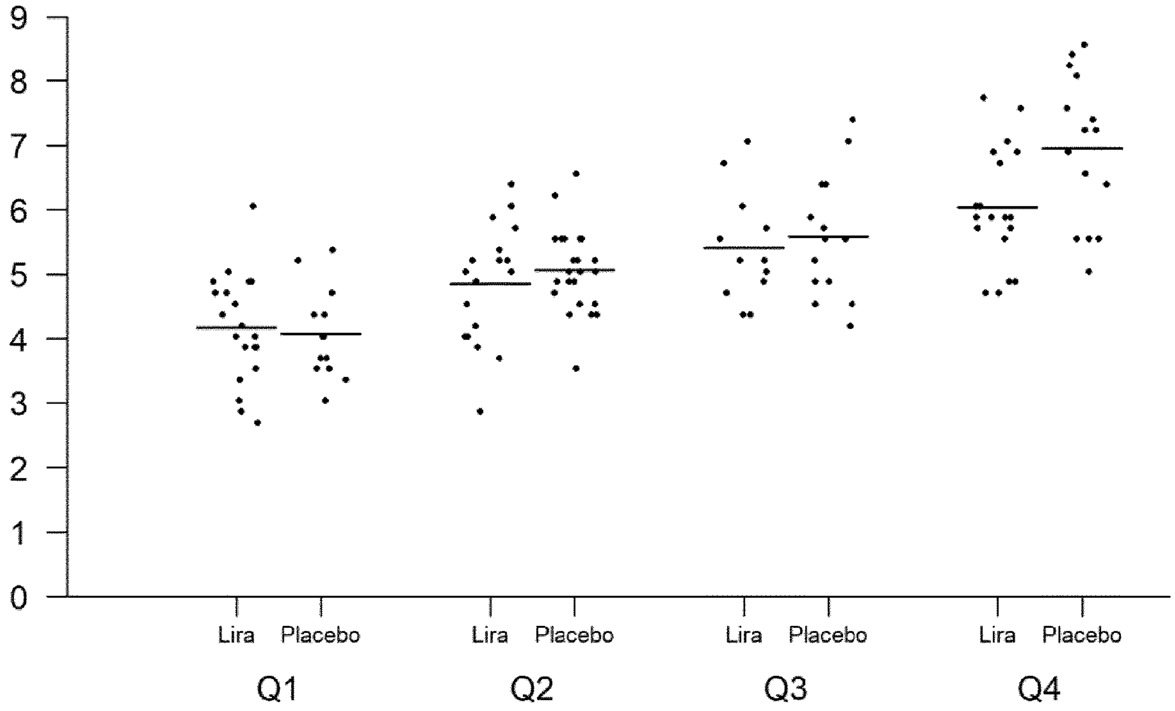
FIG. 2: Patient divided into quartiles based on serum urate level at enrolment. The figure shows the serum urate level (mg/dL) at end of the study.

In the following 52 weeks, the liraglutide group lost an additional 4.1 kg (SE 1.2, n 71) whereas the control group was almost unchanged with a weight loss of 0.2 kg (SE 1.2, n 66). Looking at the main outcome of serum urate levels change, the initial intensive diet resulted in a mean decrease of 0.21 mg/dL (95% CI 0.35 to 0.07, n 155) for the entire cohort. In the following year (week 0 to 52) the liraglutide group exhibited a further mean decrease in serum urate of 0.48 mg/dL (SE 0.11, n 69), whereas the placebo group exhibited a slight decrease in mean serum urate of 0.07 mg/dL (SE 0.12, n 65) resulting in a significant between-group difference of −0.40 mg/dL (95% CI −0.69 to −0.12, n 134)—see FIG. 1. Four participants in each group experienced serious adverse events; no deaths were observed. A subgroup analysis dividing patient into quartiles based on serum urate level at enrolment is displayed in FIG. 2. Here a clear distribution is shown where patients in the upper quartile (highest background serum urate n=34) have the largest benefit of GLP-1-RA compared to placebo controlled patients. Moreover, if treatment target is chosen to 6 mg/dL around 68% of patients in the highest urate quartile reaches that target-range in the treatment group vs 27% in the placebo group at 52 weeks of follow-up. This results in a number needed to treat (NNT) of 2.12 conservatively rounded to 3.

The respective mean weight-loss difference between Liraglutide and placebo was for the urate level quartiles (in favor of Liraglutide) going from the lowest to the highest urate-quartile; Q1 −6.95 kg (SE 2.51), Q2 −4.76 kg (SE 3.06), Q3 −2.37 (SE 2.50), Q4 −4.46 (SE 2.85).

We found in accordance with other studies, the baseline explained variance/correlation (rho-squared) between bodyweight and serum urate to be 15% (6% to 26% 0195).

Figure 3:
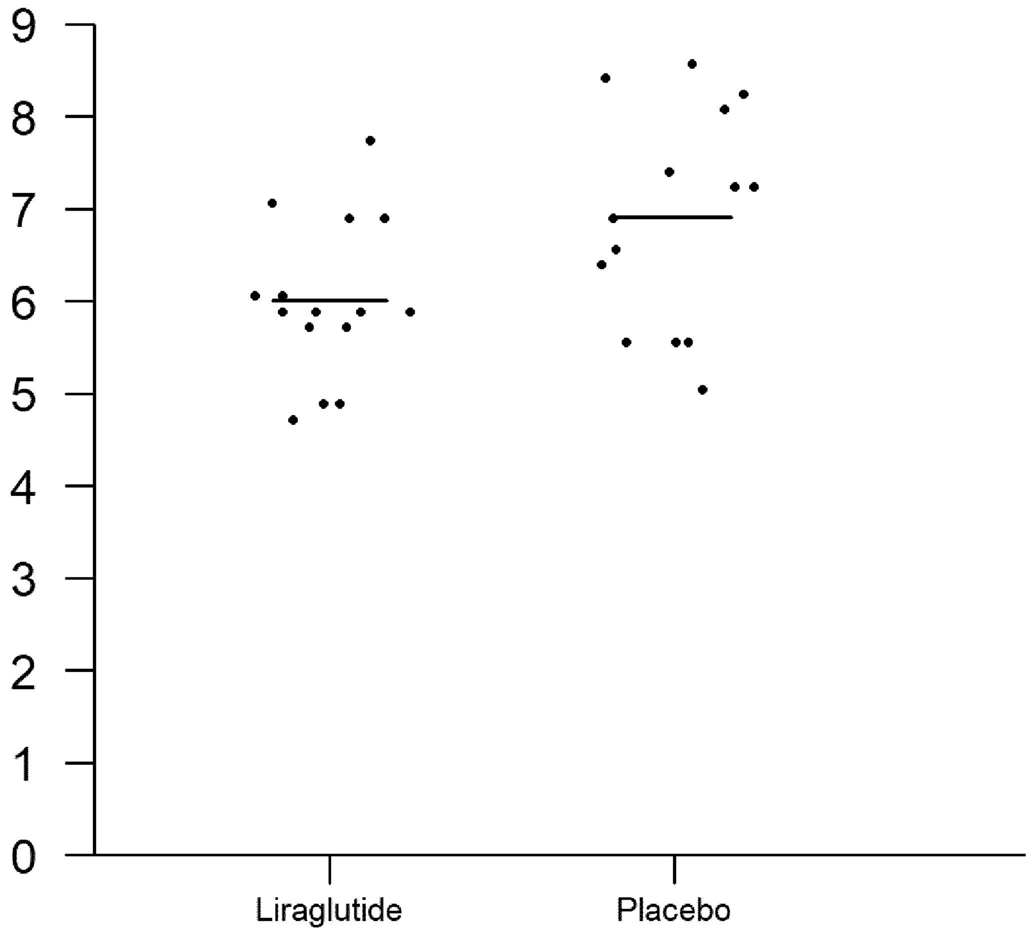
FIG. 3: The serum urate level (mg/dL) at the end of the study The figure shows the upper quartile from FIG. 2, wherein patients with concomitant type-2 diabetes (n=5) excluded; n=29 after exclusion of diabetics.

Furthermore, when excluding patients with concomitant type-2 diabetes (5 patients out of 34), the effect remained unchanged (FIG. 3). Supporting, the effect of GLP-1-RA on hyperuricemia is independent of insulin resistance and a novel effect that goes beyond what has previously been described for this group of GLP-1 receptor agonists both in terms of target population and in mode of action.

Conclusions: This secondary analysis of the LOSE-IT trial suggests that liraglutide and GLP-1 analogues in general provide an unexpected novel serum urate lowering drug mechanism in overweight patient populations with or without type-2 diabetes, with or without clinical gout during the study period. The effect is mostly predominant in the patient sample demonstrating the highest background level of serum urate at enrollment.

Compared to placebo, the differentiated effect of Liraglutide on lowering of serum urate levels is not associated with a similar differentiated weight loss for the four quartiles examined. The effect thus appears to be independent of weight loss effect of liraglutide.

Example 2, Clinical Trial of Semaglutide

Two patients with chronic gout and no diabetes where treated with another type of GLP-1 analog: Semaglutide subcutaneous (sc) once weekly.

Patient 1:

Male 55 years old, gout since more than 3 years no diabetes. Received 0.25 mg weekly for 6 weeks and then 0.5 mg twice.

Reduced s-Urate from 6.9 mg/dL to 6.0 mg/dL during a total of 8 weeks treatment VAS Pain (0-100 mm scale) from the joints was reduced from 45 mm prior to treatment to 15 mm at 8 weeks of follow-up.

No flares was observed during the treatment period, whereas gout flares was experienced 1-2 every 3 months prior to treatment No treatment emergent adverse events were experienced apart from slight nausea during the first 2 weeks.

Patient 2:

Male 63 years old, gout since more than 4 years, no diabetes. Received 0.25 mg sc for 6 weeks and 0.5 mg sc for 4 weeks.

Reduced s-Urate from 8.2 mg/dL to 7.9 mg/dL during a total of 10 weeks

VAS Pain (0-100 mm scale) from the joints was reduced from 55 mm prior to treatment to 25 mm at 10 weeks of follow-up.

No flares was observed during the treatment period, whereas gout flares was experienced 1 every 3 months prior to treatment No treatment emergent adverse events were experienced apart from slight constipation.

CONCLUSION

The two non-diabetic gout patients were treated with another class of GLP-1-analogue (semaglutide). They both lowered the serum-Urate and responded well on other parameters—supporting a class effect of GLP-1 analogues on the serum-lowering effect on urate.

Example 3, Weight Loss Through Intensive Diet Versus Dietary Guidance in Gout. A Proof of Concept Open-Label RCT Trial

Background

Our aim was to investigate whether an intensive dietary intervention can lead to substantial weight loss and induce reduction in s-Urate and other clinical benefits compared to patients receiving dietary advise as per clinical standard (control diet), in obese patients with gout.

Methods

We conducted a 16-week randomised, non-blinded, parallel-group trial in Denmark randomly assigning (1:1) people with obesity and gout to intensive low-energy diet or a control diet. The primary outcome was change in body weight. Key secondary outcomes were changes in serum urate (SU), VAS pain, and VAS fatigue. The trial is pre-registered with ClinicalTrials.gov, NCT03664167.

Findings 61 participants were randomly assigned to intensive diet (n=29) or control diet (n=32). Participants had a mean age of 60.3 (SD, 9.9) years, mean BMI of 35.6 (SD, 5.0) kg/m$^2$, and 59 (97%) were men. In the intention-to-treat population, there was a statistically and clinically significant difference in change in body weight from baseline to 16 weeks between the diet and control groups (−15.4 kg vs −7.7 kg; difference: −7.7 kg [95% Cl −10.7, −4.7], p<0.001). Surprisingly, no statistically significant differences in changes in SU, VAS fatigue, or VAS pain were observed between groups. Slightly more flares were reported in the intensive diet group. No serious adverse events or deaths were reported.

Changes in primary and secondary endpoints after 16 weeks

| | n | Intensive diet group | n | Control diet group | Difference between groups | P-value |
|---|---|---|---|---|---|---|
| Body weight, kg | 29 | −15.4 (0.7) | 32 | −7.7 (0.7) | −7.7 (−10.7 to −4.7) | <0.001 |
| Key secondary outcomes | | | | | | |
| Serum urate, mg/dL | 29 | −0.6 (0.2) | 32 | −0.3 (0.2) | −0.3 (−0.9 to 0.3) | 0.744 |
| VAS Fatigue (0-100) | 28 | −17.4 (3.9) | 31 | −8.6 (4.3) | −8.8 (−25.5 to 7.9) | 0.655 |
| VAS Pain (0-100) | 28 | −2.5 (4.9) | 31 | −12.5 (5.4) | 9.9 (−11.1 to 31.0) | 0.748 |

Interpretation

An intensive dietary intervention effectively lowered body weight in obese people with gout. However, despite a significant weight loss there was no statistical difference on effects on S-Urate, fatigue, and pain compared to patients receiving standard dietary advise. This supports that the serum urate lowering effect of GLP-1 analogue's are effects demonstrated outside the known weight losing effects.

REFERENCES

1 Richette P et al. 2016. Ann Rheum Dis 2017; 76:29-42.
2 Nielsen S M et al. Ann Rheum Dis 2017 76(11):1870-1882.
3 Gudbergsen H et al. BMJ 2019.71-2.

The invention claimed is:

1. A method for treatment of hyperuricemia in a normoglycemic subject having a serum level of uric acid above 6 mg/dL prior to initiation of treatment, the method comprising administering a glucagon-like peptide-1 (GLP-1) receptor agonist to subject for at least 8 weeks, said glucagon-like peptide-1 receptor agonist selected from the group consisting of exenatide, liraglutide, lixisenatide, albiglutide, dulaglutide, semaglutide, and combinations thereof, wherein a said serum level of uric acid is reduced by at least 0.1 mg/dL over the 8 weeks.

2. The method of claim 1, wherein the subject has a normal HbAic level.

3. The method of claim 1, wherein the subject has a fasting glucose level below 7.0 mmol/L.

4. The method of claim 2, wherein the subject has a HbAic level below 48 mmol/mol.

5. The method of claim 1, wherein the GLP-1 receptor agonist is semaglutide or liraglutide.

6. The method of claim 1, wherein the subject suffers from gout.

7. The method of claim 1, wherein the subject is overweight or obese.

8. The method of claim 1, wherein the subject has reduced kidney function as indicated by an abnormal estimated glomerular filtration rate measurement or has osteoarthrosis.

9. The method of claim 1, wherein the subject is or has been treated with a xanthine oxidoreductase inhibitor (XOI).

10. The method of claim 9, wherein the subject is hypersensitive to XOI therapy or does not respond to XOI therapy.

11. The method of claim 9, wherein the XOI is allopurinol.

12. The method of claim 1, wherein the subject has a serum level of uric acid above 6.5 mg/dL prior to initiation of treatment.

13. The method of claim 1, wherein a uric acid level is reduced by at least 0.21 mg/dL over 8 weeks.

14. The method of claim 1, wherein the administering reduces joint pain, joint effusion, deposits of uric acid crystals, or deposition of uric acid in joints.

15. The method of claim 1, wherein the glucagon-like peptide-1 receptor agonist is liraglutide and a dosage is from 1 to 3 mg once per day.

16. The method of claim 1, wherein the glucagon-like peptide-1 receptor agonist is semaglutide and a dosage is from 0.25 to 5 mg weekly.

17. The method of claim 1, wherein the glucagon-like peptide-1 receptor agonist is administered subcutaneously or orally.

18. A method for treatment of hyperuricemia in a normoglycemic subject having a serum level of uric acid above 6 mg/dL prior to initiation of treatment, the method comprising administering tirzepatide to said subject for at least 8 weeks, wherein the serum level of uric acid is reduced by at least 0.1 mg/dL over the 8 weeks.

* * * * *